United States Patent
Ahn et al.

(10) Patent No.: US 11,395,911 B2
(45) Date of Patent: Jul. 26, 2022

(54) SKIN TREATMENT NEEDLE WITH ENERGY UNIFORMITY CORRUGATIONS AND SKIN TREATMENT DEVICE

(71) Applicant: AGNES MEDICAL CO., LTD., Seongnam-si (KR)

(72) Inventors: Gunyoung Ahn, Seongnam-si (KR); Wooseok Koh, Seoul (KR)

(73) Assignee: AGNES MEDICAL CO., LTD., Seongnam-si (KR)

(*) Notice: Subject to any disclaimer, the term of this patent is extended or adjusted under 35 U.S.C. 154(b) by 451 days.

(21) Appl. No.: 16/475,872

(22) PCT Filed: Nov. 16, 2018

(86) PCT No.: PCT/KR2018/014103
§ 371 (c)(1),
(2) Date: Jul. 3, 2019

(87) PCT Pub. No.: WO2020/101083
PCT Pub. Date: May 22, 2020

(65) Prior Publication Data
US 2021/0353933 A1 Nov. 18, 2021

(30) Foreign Application Priority Data
Nov. 16, 2018 (KR) .......................... 10-2018-0141580

(51) Int. Cl.
*A61N 1/05* (2006.01)
*A61N 1/32* (2006.01)
(Continued)

(52) U.S. Cl.
CPC ............ *A61N 1/0502* (2013.01); *A61N 1/328* (2013.01); *A61N 1/36017* (2013.01); *H01B 3/307* (2013.01)

(58) Field of Classification Search
CPC ... A61N 1/0502; A61N 1/328; A61N 1/36017
See application file for complete search history.

(56) References Cited

U.S. PATENT DOCUMENTS

| | | | |
|---|---|---|---|
| 2003/0060856 A1* | 3/2003 | Chornenky | A61B 18/1492 607/40 |
| 2011/0018441 A1 | 7/2011 | Greep et al. | |
| 2011/0184410 A1* | 7/2011 | Greep | A61B 18/1402 606/45 |

FOREIGN PATENT DOCUMENTS

| | | |
|---|---|---|
| KR | 10-2013-0012805 A | 2/2013 |
| KR | 10-2013-0045581 A | 5/2013 |

(Continued)

OTHER PUBLICATIONS

English translation of KR-101301807-B1 published on Apr. 16, 2013 (Year: 2013).*

(Continued)

*Primary Examiner* — Unsu Jung
*Assistant Examiner* — Adreanne A. Arnold
(74) *Attorney, Agent, or Firm* — Paratus Law Group, PLLC

(57) ABSTRACT

Disclosed is a skin treatment needle by which energy is supplied into skin tissue to increase the speed of skin regeneration. The skin treatment needle includes a needle body that is formed of a conductive material and inserted into skin, starting from a front end thereof. A region of an outer circumferential surface of the needle body includes a conductive portion which is a region inducing an electric field different from those formed at other portions of the needle body, and the conductive portion includes a plurality of corrugations to cause an electric field formed via the conductive portion to have a uniform distribution without being biased and concentrated to a side.

12 Claims, 19 Drawing Sheets

(51) Int. Cl.
*A61N 1/36* (2006.01)
*H01B 3/30* (2006.01)

(56) References Cited

FOREIGN PATENT DOCUMENTS

| KR | 10-1301807 B1 | 8/2013 |
| KR | 10-1304423 B1 | 9/2013 |
| KR | 10-2018-0078026 A | 7/2018 |
| WO | WO 2016/161201 A2 | 10/2016 |

OTHER PUBLICATIONS

English translation of KR-1020130049991 published May 15, 2013 (Year: 2013).*
English translation of KR 01-301807 B1 published on Apr. 16, 2013 (Year: 2013).*
English translation of KR-10-1304423 B1 published May 15, 2013 (Year: 2013).*
International Search Report for PCT/KR2018/014103 dated Aug. 5, 2019 from Korean Intellectual Property Office.
Korean Office Action for related KR Application No. 10-2018-0141580 dated May 20, 2020 from Korean Intellectual Property Office.
Korean Notice of Allowance for related KR Application No. 10-2018-0141580 dated Jan. 12, 2021 from Korean Intellectual Property Office.

* cited by examiner

SKIN TREATMENT NEEDLE WITH ENERGY UNIFORMITY CORRUGATIONS AND SKIN TREATMENT DEVICE

CROSS-REFERENCE TO PRIOR APPLICATIONS

This application is a National Stage patent application of PCT International Patent Application No. PCT/KR2018/014103 (filed on Nov. 16, 2018) under 35 U.S.C. § 371, which claims priority to Korean Patent Application No. 10-2018-0141580 (filed on Nov. 16, 2018), which are all hereby incorporated by reference in their entirety.

ACKNOWLEDGEMENTS

This work was supported by Institute of Information & communications Technology Planning & Evaluation (IITP) grant funded by the Korea government (MSIT) (No. 2018-0-00957, Development of multiple frequency 3D Fractional RF devices for wrinkle treatment and various skin diseases).

BACKGROUND

The present invention relates to a skin treatment needle, and more particularly, to a skin treatment needle capable of minimizing damage to an epidermal layer, supplying energy to various depths of the skin according to a purpose of treatment, and achieving a uniform distribution of energy supplied without being excessively concentrated, thereby increasing the speed of skin regeneration and shortening a treatment period, and a skin treatment device.

Generally, the skin covering the entire human body is largely divided into three layers, i.e., an epidermal layer, a dermal layer, and a subcutaneous fat layer.

Among these layers, the epidermal layer is the outermost layer of the skin, includes various layers, such as a horny layer, a transparent layer, a granular layer, a spinous layer, and a basal layer, according to the position and function thereof, and has protection, defense and secretion functions.

The dermal layer is located below the epidermal layer and adjacent to the basal layer, forms a great part of the skin, and includes a papillary layer which contains moisture, protein, saccharides, mucopolysaccharides, minerals and inorganic salts in the form of jelly and at which capillaries related to blood circulation and lymph vessels carrying lymph are located, and a reticular layer containing collagen which is collagen fibers related to the wrinkles of the skin, elastin which is elastic fibers giving elasticity to the skin, and a matrix (a reservoir of water).

In recent years, much attention has been paid to a skin treatment method of maintaining skin elasticity and minimizing skin aging by directly transmitting energy such as high-frequency current to the dermal layer of the skin through needles to activate cellular tissues.

Examples of such a skin treatment method include Korean Patent Laid-Open Publication No. 2013-0012805 (Feb. 5, 2013) disclosing a skin treatment device using high-frequency energy, the skin treatment device including a high-frequency generator, a plurality of needles providing high-frequency energy generated by the high-frequency generator into the skin, a driving part providing power to insert the needles into the skin, and a controller controlling the driving part to insert ends of the needles to a first target position in the skin and move the needles to a second target position while the needles are inserted into the skin.

However, the skin treatment device of the related art has a problem that high-frequency energy is transmitted via a single electrode needle to not only the dermal layer but also the epidermal layer, thereby causing damage to the epidermal layer.

In order to solve the above problem of the related art, a needle in which an insulating film is applied on a surface thereof and only a portion of a lower end of the insulating film is removed to supply energy thereby has been developed. However, energy can be locally supplied only via the lower end of the needle when the needle is configured as described above and thus cannot be supplied to various depths of the skin as required according to a purpose of treatment.

SUMMARY

The present invention is directed to a skin treatment needle capable of minimizing damage to an epidermal layer, supplying energy to various depths of the skin according to a purpose of treatment, and achieving a uniform distribution of energy supplied without being excessively concentrated, thereby increasing the speed of skin regeneration and shortening a treatment period, and a skin treatment device.

One aspect of the present invention provides a skin treatment needle by which energy is supplied into skin tissue to increase the speed of skin regeneration, the skin treatment needle including a needle body that is formed of a conductive material and inserted into skin, starting from a front end thereof. A region of an outer circumferential surface of the needle body includes a conductive portion which is a region inducing an electric field different from those formed at other portions of the needle body. The conductive portion includes a plurality of corrugations to cause an electric field formed via the conductive portion to have a uniform distribution without being biased and concentrated to a side.

The skin treatment needle may further include an insulating film coated with an insulating material, the insulating film being provided on a remaining portion of the outer circumferential surface of the needle body aside from the conductive portions.

The insulating film may be formed of parylene or Teflon.

The skin treatment needle may further include concave portions formed by micromachining etching a remaining portion of the outer circumferential surface of the needle body, aside from a portion at which the conductive portion is to be formed, to form the conductive portion in a protruding form, the concave portion being relatively recessed. A plurality of conductive portions identical to the conductive portion and a plurality of concave portions identical to the concave portion may be alternately arranged in a longitudinal direction of the needle body, the plurality of conductive portions and the plurality of concave portions each having a longitudinal width of 100 to 300 micrometers. A depth of corrugation valleys formed in the plurality of conductive portions may be in a range of 5 to 15 micrometers.

The conductive portion may be formed to be recessed by micromachining etching the outer circumferential surface of the needle body, wherein the conductive portion may be provided with a plurality of conductive portions that are arranged to be spaced apart from each other in the longitudinal direction of the needle body. A depth of corrugation valleys formed in the conductive portions may be in a range of 5 to 15 micrometers.

The conductive portion may be provided with one conductive portion or a plurality of conductive portions which may be arranged to be spaced part from each other on the outer circumferential surface of the needle body from the front end of the needle body to a rear end thereof.

The conductive portions may be provided in a 360-degree circumferential direction of the outer circumferential surface of the needle body.

The conductive portions may be provided on the outer circumferential surface of the needle body only in one direction to have directionality.

The conductive portions may be provided with a plurality of conductive portions which are spaced apart from each other on the outer circumferential surface of the needle body and a depth of corrugation valleys may increase toward the front end of the needle body from a rear end thereof to form a stronger electric field as a depth of insertion into the skin increases.

The corrugations may include concave semicircular corrugation valleys consecutively formed and connecting lines between the corrugation valleys to form a high-intensity electric field at a plurality of positions via the connecting lines, the connecting lines having a sharply protruding form.

The corrugation valleys may be formed by performing micromachining etching, the corrugation valleys having a depth of less than or equal to ¼ of a diameter of the needle body.

The depth of the corrugation valleys may be in a range of 5 to 15 micrometers.

Another aspect of the present invention provides a skin treatment device including a support member and a plurality of needles, the plurality of needles being provided at a lower portion of the support member to be inserted into skin, starting from front ends thereof.

Another aspect of the present invention provides a skin treatment device including a support member and a plurality of needles provided at a lower portion of the support member to be inserted into skin, starting from front ends thereof. Each of the plurality of needles includes a needle body that is formed of a conductive material and inserted into skin, starting from a front end thereof. A region of an outer circumferential surface of the needle body includes a conductive portion which is a region inducing an electric field different from those formed at other portions of the needle body. The conductive portion includes a plurality of corrugations to cause an electric field formed via the conductive portion to have a uniform distribution without being biased and concentrated to a side. The plurality of needles include directional needles, in which the conductive portions are provided only in one direction of the outer circumferential surface of the needle body to have directionality. The directional needles are provided around a center of an installation surface of the support member such that the conductive portion faces the center of the installation surface of the support member.

The plurality of needles may include the directional needles and non-directional needles including the conductive portions provided along the outer circumferential surface of the needle body in a 360-degree circumferential direction. The non-directional needles may be provided at the center of the installation surface of the support member.

Each of the directional needles and the non-directional needles may include an insulating film coated with an insulating material, the insulating film being provided on a remaining portion of the outer circumferential surface of the needle body aside from the conductive portion.

In the non-directional needles among the directional needles and the non-directional needles, the conductive portion is provided with a plurality of conductive portions that may be provided on the outer circumferential surface of the needle body to be spaced apart from each other, and a longitudinal width of the plurality of conductive portions and a depth of corrugation valleys may increase from a rear end of the needle body toward a front end thereof to form a stronger electric field as a depth of insertion into the skin increases.

A skin treatment needle and a skin treatment device according to the present invention are capable of minimizing damage to an epidermal layer and uniformly supplying energy to various depths of the skin according to a purpose of treatment without being excessively concentrated, thereby increasing the speed of skin regeneration and shortening a treatment period.

DETAILED DESCRIPTION

Figure 1:
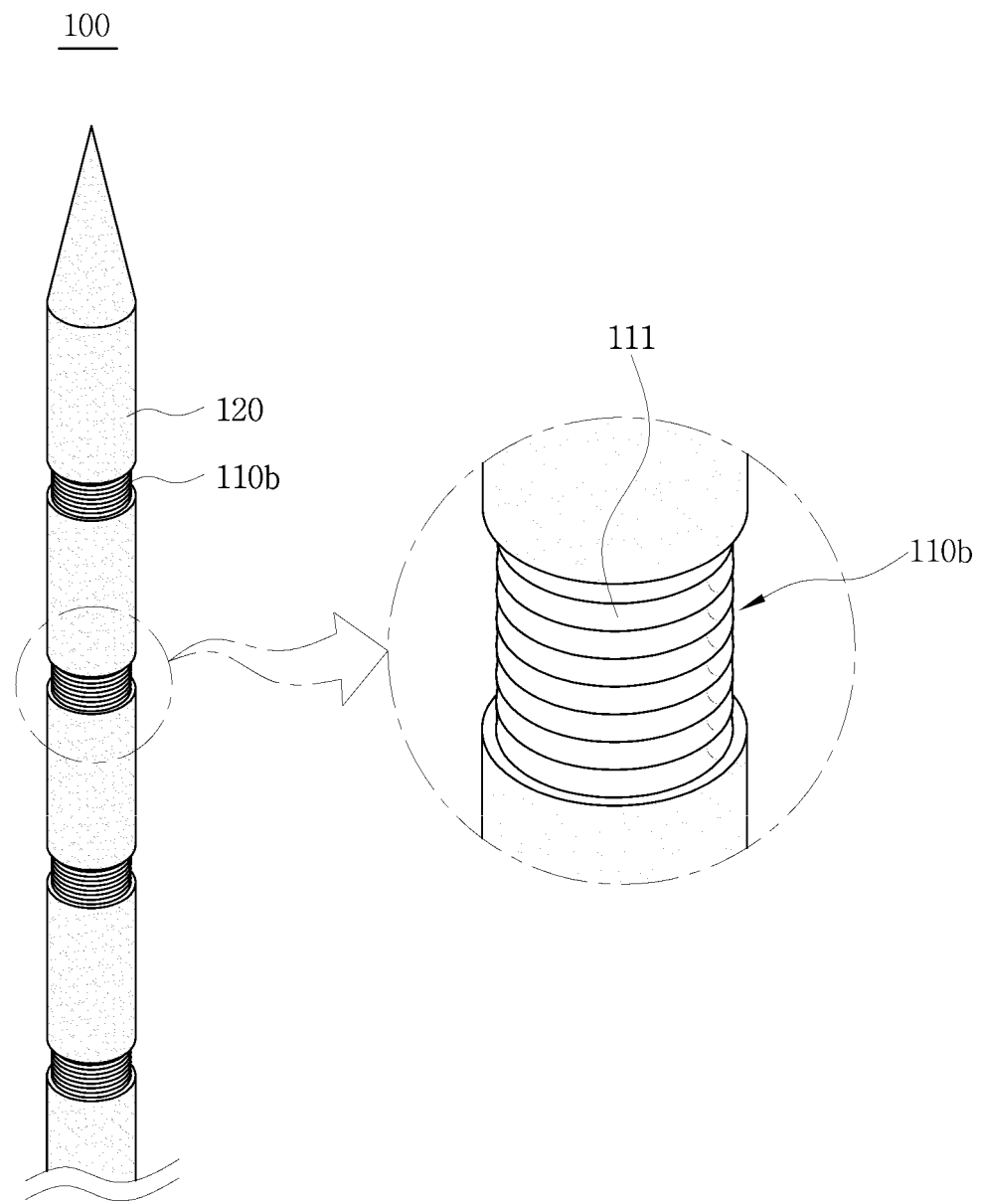
FIG. 1 is a perspective view of a skin treatment needle according to a first embodiment of the present invention.

A skin treatment needle and a skin treatment device according to embodiments of the present invention will be described in detail with reference to the accompanying drawings below. Various modifications may be made in the present invention and the present invention may be embodied in many different forms. Thus, exemplary embodiments are illustrated in the drawings and described herein in detail. It should be understood that the present invention is not limited to the embodiments set forth herein and is to cover all modifications, equivalents, and alternatives falling within the spirit and scope of the present invention. Like reference numerals are used for like elements in describing each drawing. In the accompanying drawings, structures may be exaggerated in size for clarity or illustrated to be smaller than actual sizes thereof to help understand a schematic configuration.

As used herein, terms such as "first" and "second" may be used to describe various elements but the elements should not be understood as being limited by these terms. The terms are used only for the purpose of distinguishing one element from another. For example, a first component could be termed a second component without departing from the scope of the present invention, and similarly, a second component could also be termed a first component. On the other hand, unless otherwise defined, all terms used herein, including technical or scientific terms, have the same meaning as commonly understood by one of ordinary skill in the art to which the present invention pertains. It will be understood that terms, such as those defined in commonly used dictionaries, should be interpreted as having a meaning that is consistent with their meaning in the context of the relevant art and will not be interpreted in an idealized or overly formal sense unless expressly so defined herein.

First Embodiment

Figure 2:
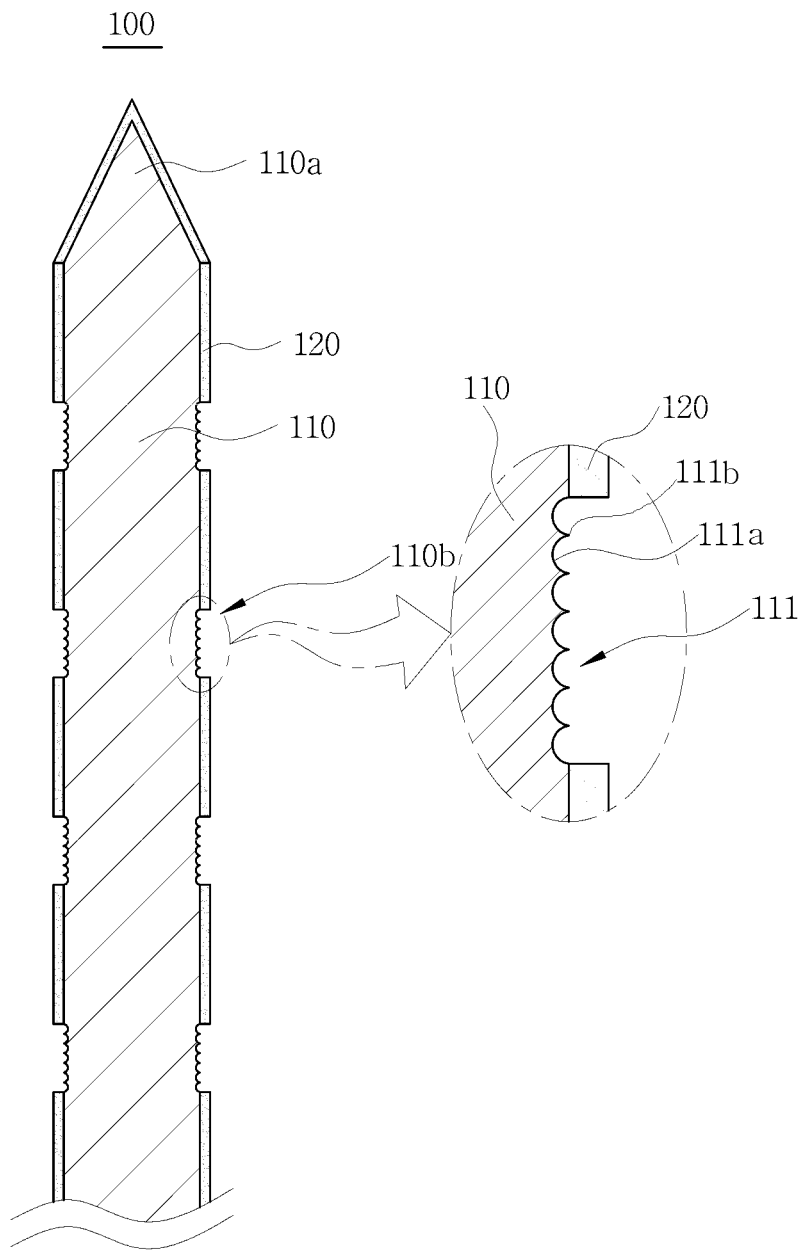
FIG. 2 is a longitudinal sectional view for explaining a configuration of the skin treatment needle according to the first embodiment of the present invention.

FIG. 1 is a perspective view of a skin treatment needle according to a first embodiment of the present invention. FIG. 2 is a longitudinal sectional view for explaining a structure of the skin treatment needle according to the first embodiment of the present invention.

As illustrated in the drawings, a skin treatment needle 100 according to the first embodiment of the present invention includes a needle body 110, and an insulating film 120 coated with a harmless insulating material, such as parylene or Teflon, to cover an outer surface of the needle body 110.

A region of the insulating film 120 is removed by micromachining etching to form a conductive portion 110b different from other portions of the insulating film 120. The conductive portion 110b is provided with a plurality of corrugations 111 formed by micromachining etching the needle body 110.

The conductive portion 110b is differentiated from the other parts of the needle body 110 coated with the insulating film 120 and thus a relatively strong electric field may be formed thereby to supply higher energy to the skin. Furthermore, because the conductive portion 110b is provided with the corrugations 111, a uniform distribution of electric field is formed at the conductive portion 110b without being biased and concentrated to a side. An effect obtained by forming the corrugations 111 will be described in detail below.

One conductive portion 110b may be provided on an outer circumferential surface of the needle body 110 from a front end 110a of the needle body 110 to a rear end thereof according to a purpose of treatment, but a plurality of conductive portions 110b are preferably provided to be spaced apart from each other as illustrated in the drawings. The conductive portion 110b is provided along the outer circumferential surface of the needle body 110 in a 360-degree circumferential direction, as illustrated in the drawings. When a plurality of conductive portions 110b are provided on the outer circumferential surface of the needle body 110 in the 360-degree circumferential direction, energy may be supplied to skin tissue in a substantially omnidirectional manner by simultaneously forming electric fields at a plurality of points in the skin into which the skin treatment needle 100 is inserted.

The corrugations 111 are formed by micromachining etching the region of the conductive portion 110b of the needle body 110. The corrugations 111 include concave semicircular corrugation valleys 111a which are consecutively formed. Connecting lines 111b between the corrugation valleys 111a protrude sharply as illustrated in an enlarged part of FIG. 2. When the corrugations 111 include convex semicircular protrusions which are consecutively formed instead of the concave semicircular corrugation valleys 111a which are consecutively formed, the connecting lines 111b are not formed in a sharp protruding form.

Figure 3:
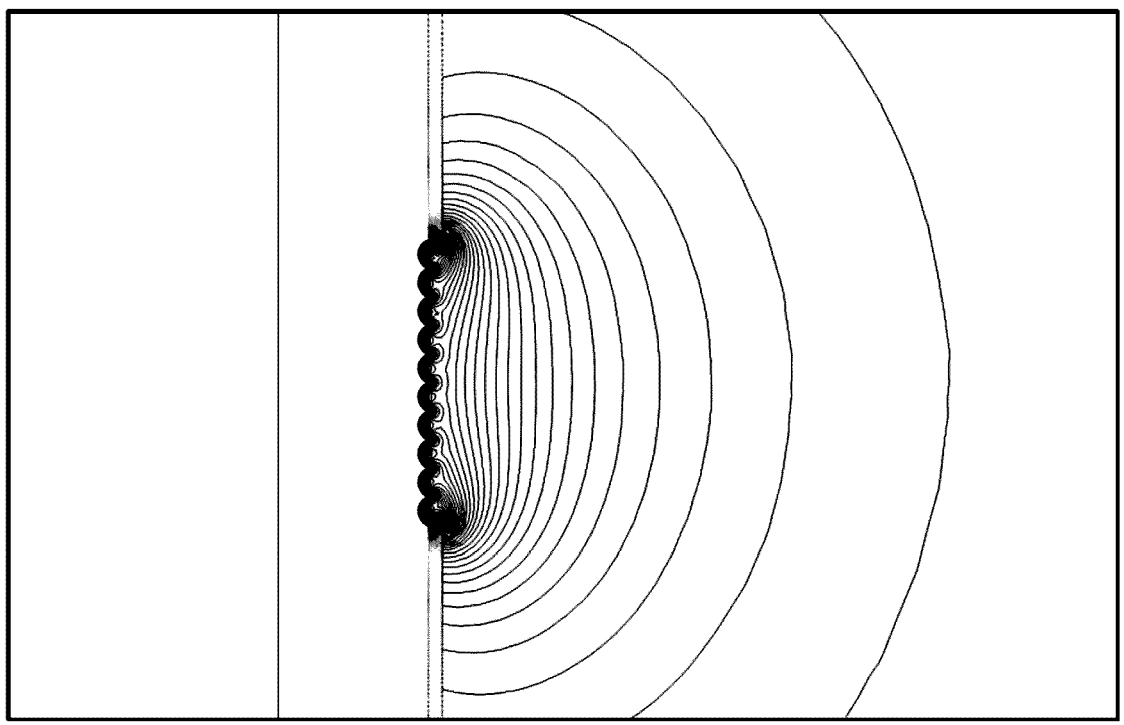
FIG. 3 is a graph showing an electric field distribution of a corrugated conductive portion of the skin treatment needle according to the first embodiment of the present invention.
Figure 4:
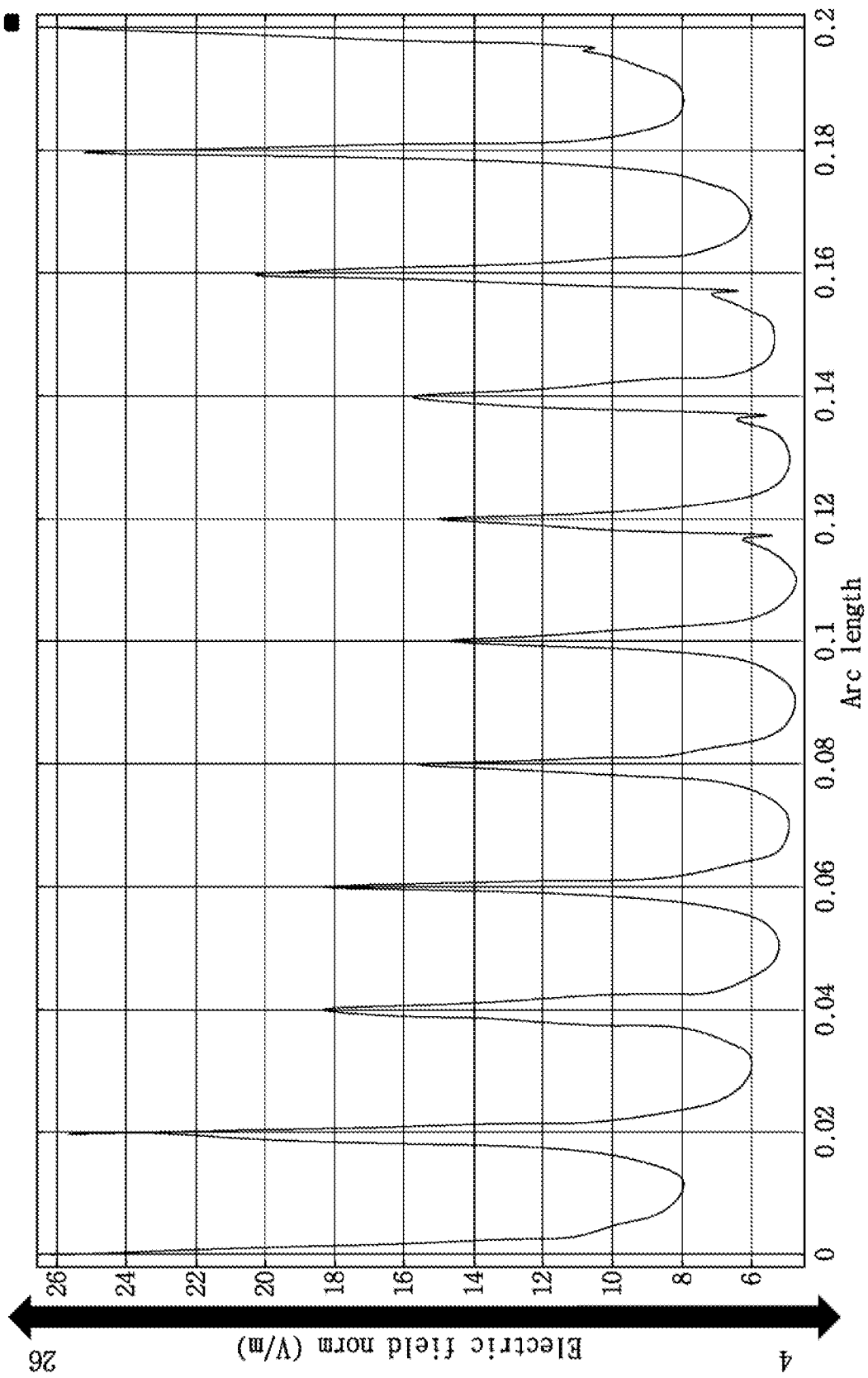
FIG. 4 is a graph showing an electric field norm distribution of the corrugated conductive portion of the skin treatment needle according to the first embodiment of the present invention.

According to the configuration of the present invention described above, because an electric field tends to be concentrated mainly on angled corners, a stronger electric field may be formed around the connecting line 111b which sharply protrudes due to the concave semicircular corrugation valleys 111a. There are a plurality of connecting lines 111b between the corrugation valleys 111a even in a region of one conductive portion 110b and thereby a substantially uniform distribution of a high electric field may be obtained as shown in the graphs of FIGS. 3 and 4. Accordingly, strong, uniform and high-quality energy may be supplied into the skin.

Figure 5:
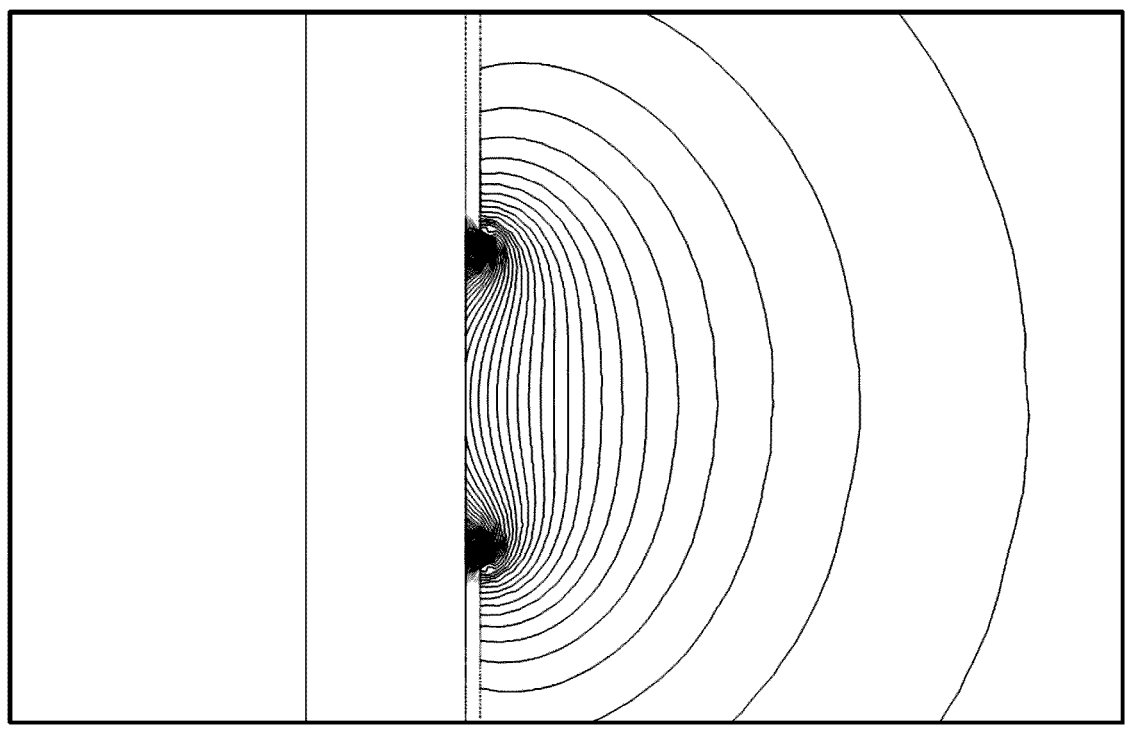
FIG. 5 is a graph showing an electric field distribution of a non-corrugated conductive portion of a skin treatment needle according to a comparative example.
Figure 6:
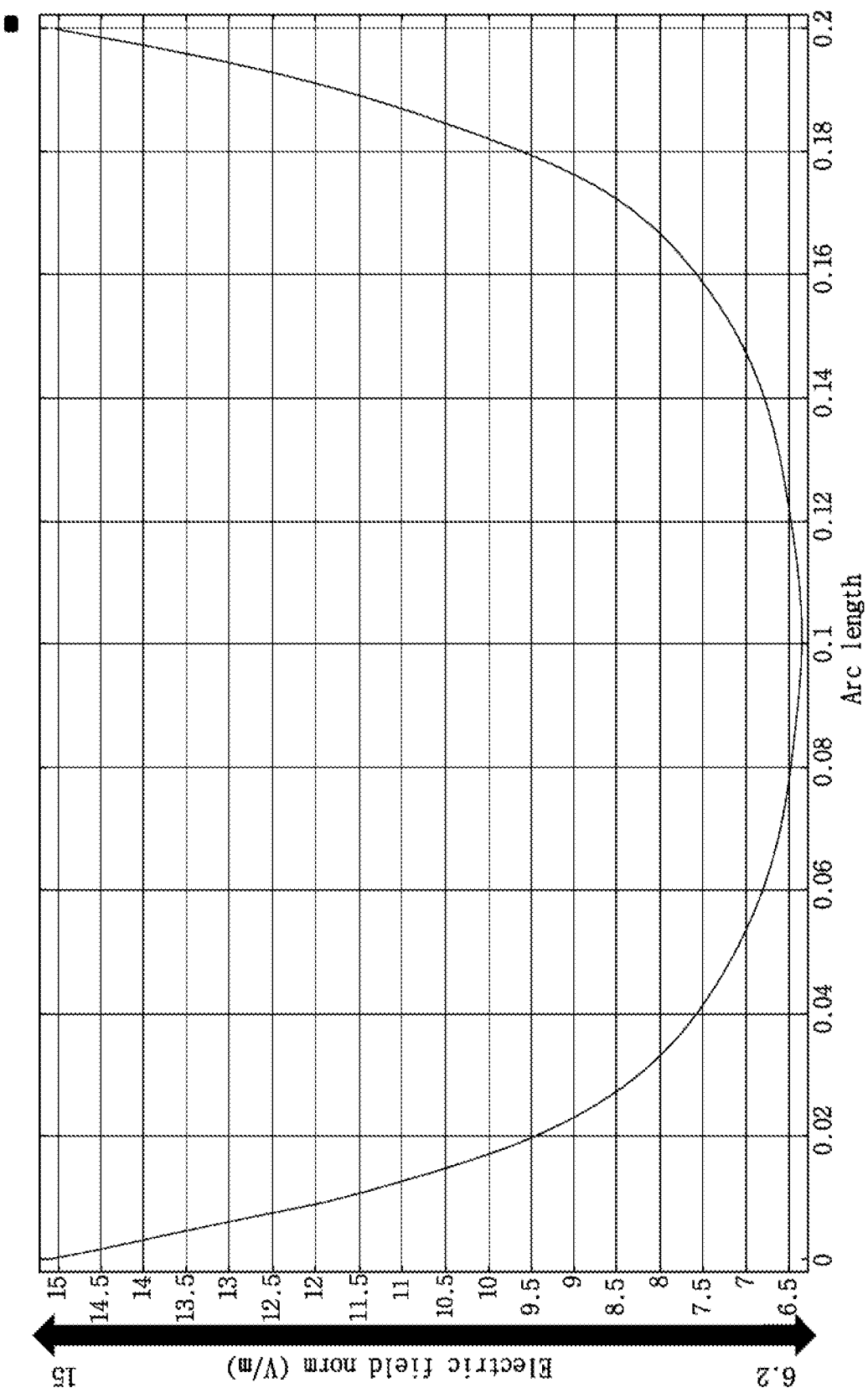
FIG. 6 is a graph showing an electric field norm distribution of the non-corrugated conductive portion of the skin treatment needle according to the comparative example.
Figure 7:
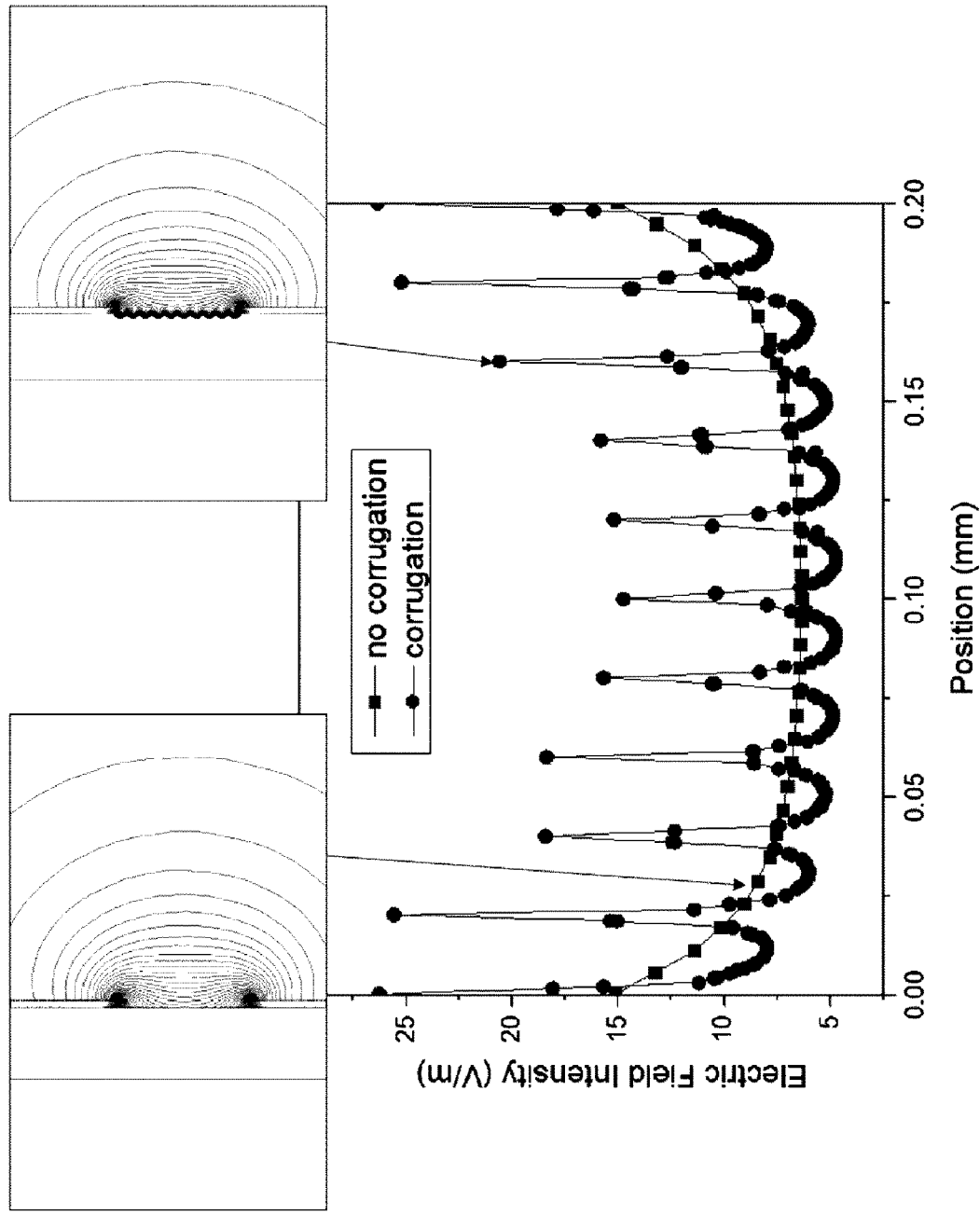
FIG. 7 is a graph comparing the intensity of an electric field formed via the conductive portion of the skin treatment needle according to the first embodiment with that of an electric field formed via the conductive portion of the skin treatment needle according to the comparative example.

Unlike the first embodiment of the present invention, as shown in FIGS. 5 and 6, in the case of a needle of a comparative example which is provided with only a conductive portion without the corrugations 111, an electric field is excessively concentrated only at angled ends of the conductive portion due to the conductive portion and the intensities of the electric field at the other parts of the needle are extremely low, and thus, generally, the electric field is not uniformly distributed. Referring to FIG. 7 comparing the first embodiment with the comparative example, an action and effect of the corrugations 111 of the first embodiment of the present invention were remarkable. Referring to FIG. 7, an intensity of an electric field generated via the conductive portion 110b with the corrugations 110b of the first embodiment was far higher than that of an electric field generated via the conductive portion having no corrugations of the comparative example, and a distribution of the electric field at the conductive portion 110b was overall uniform.

Thus, an electric field may be uniformly formed by the needle having the conductive portion 110b with the corrugations 111 according to the first embodiment of the present invention and thereby the intensity and amount of energy to be supplied into the skin may be more easily controlled. Accordingly, a high-quality skin treatment may be implemented.

Here, the corrugation valleys 111a of the corrugations 111 are formed by micromachining etching to have a depth of ¼ or less of a diameter of the needle body 110. More specifically, the depth of the corrugation valleys 111a is preferably in a range of 5 to 15 micrometers, taking into account the diameter of the needle body 110. The needle body 110 is likely to break when the depth of the corrugation valleys 111a of the corrugations 111 exceeds half of the diameter of the needle 100. The intensity of an electric field at the conductive portion 110b is significantly different from those of electric fields at other portions of the needle body 110 when the depth of the corrugation valleys 111a of the corrugations 111 is less than 5 micrometers, thereby making it difficult to form an electric field at a sufficient level.

The front end 110a of the needle body 110 is formed in a pointed shape to be easily inserted into the skin, and is preferably coated with the insulating film 120. However, because the needle body 110 is formed to have a thin thickness, the front end 110a need not necessarily be formed in the pointed shape to be inserted into the skin, and the front end 110a need not necessarily be coated with the insulating film 120. However, the rear end of the needle body 110 is preferably coated with the insulating film 120 to protect the epidermal layer of the skin. This is because it is preferable that energy not be supplied using an electric field to the epidermal layer of the skin exposed to an external environment, so that a regeneration period after a skin treatment may be shortened and skin wounds that may occur in the epidermal layer after the skin treatment may be prevented from being exposed to the outside during the regeneration period.

Although the needle body 110 is illustrated in the drawings as being formed solidly, the needle body 110 may be hollow for the purpose of drug injection or the like. The needle body 110 preferably has a cylindrical shape as illustrated in the drawings but is not limited thereto and may have a prism shape having a polygonal cross section. In particular, in the case of a directional needle to be described with respect to a second embodiment below, a needle body having a prism shape may be preferable.

Figure 8:
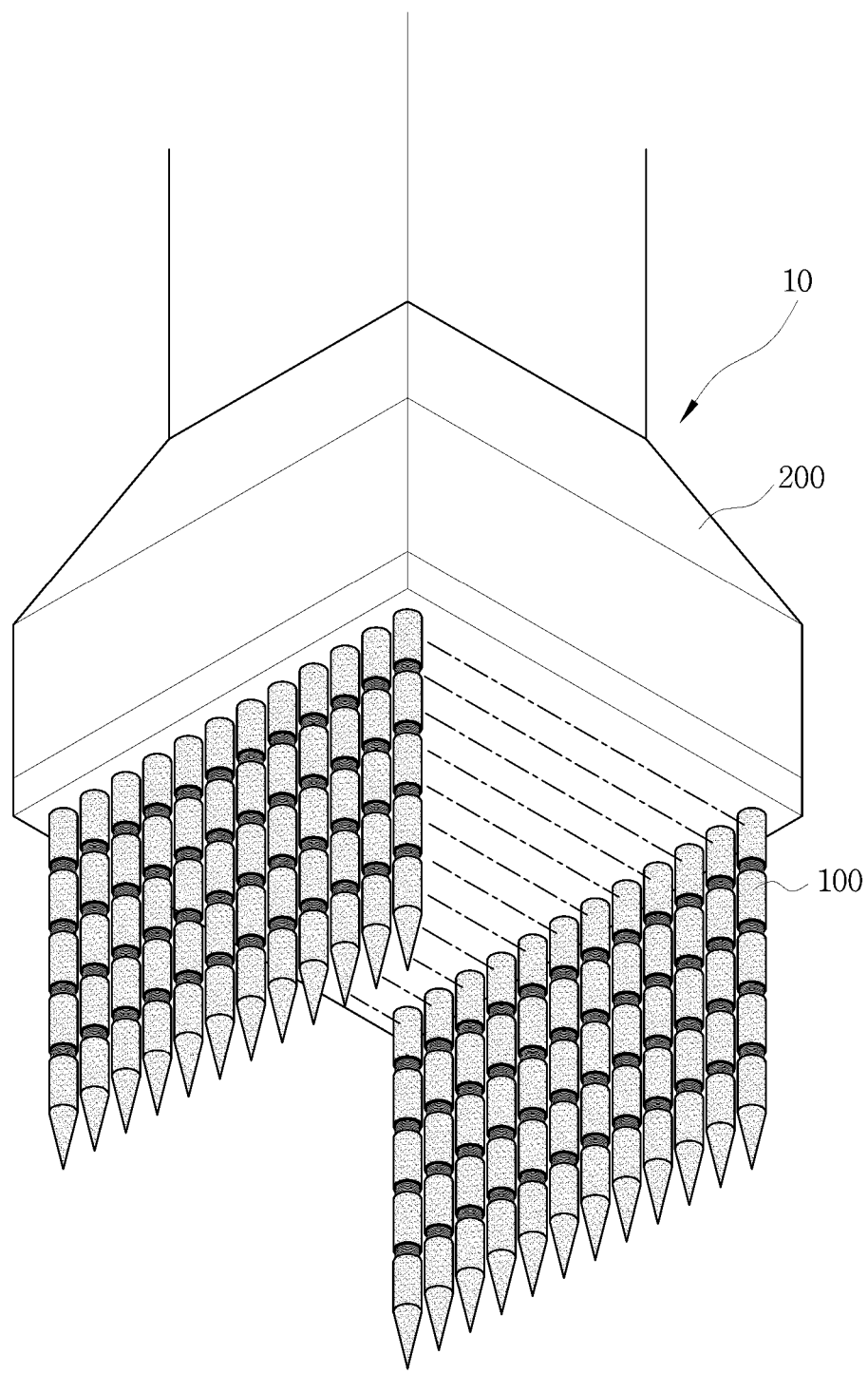
FIG. 8 is a perspective view for explaining a skin treatment device to which skin treatment needles according to the first embodiment are applied.

FIG. 8 is a perspective view for explaining a skin treatment device to which skin treatment needles according to the first embodiment are applied.

As illustrated in the drawings, the skin treatment device to which the skin treatment needles 100 according to the first embodiment of the present invention are applied includes a support member 200, and a needle array of needles 100 of the first embodiment described above.

The support member 200 includes several components to receive power and supply the power to the needle body 110. The components of the support member 200 are well known and thus a detailed description thereof will be omitted here.

Although it is illustrated in the drawing that the needle array is installed by aligning the needles 100 in two rows on both sides of a lower portion of the support member 200, the needle array is not limited thereto and may be configured by variously arranging a plurality of needles 100. In particular, the skin treatment needles 100 of the first embodiment are substantially omni-directional needles in terms of formation of a magnetic field, in which the conductive portion 110b and the corrugations 111 are provided on the outer circumferential surface of the needle body 110 in the 360-degree circumferential direction, and thus may be arranged relatively freely.

Figure 9:
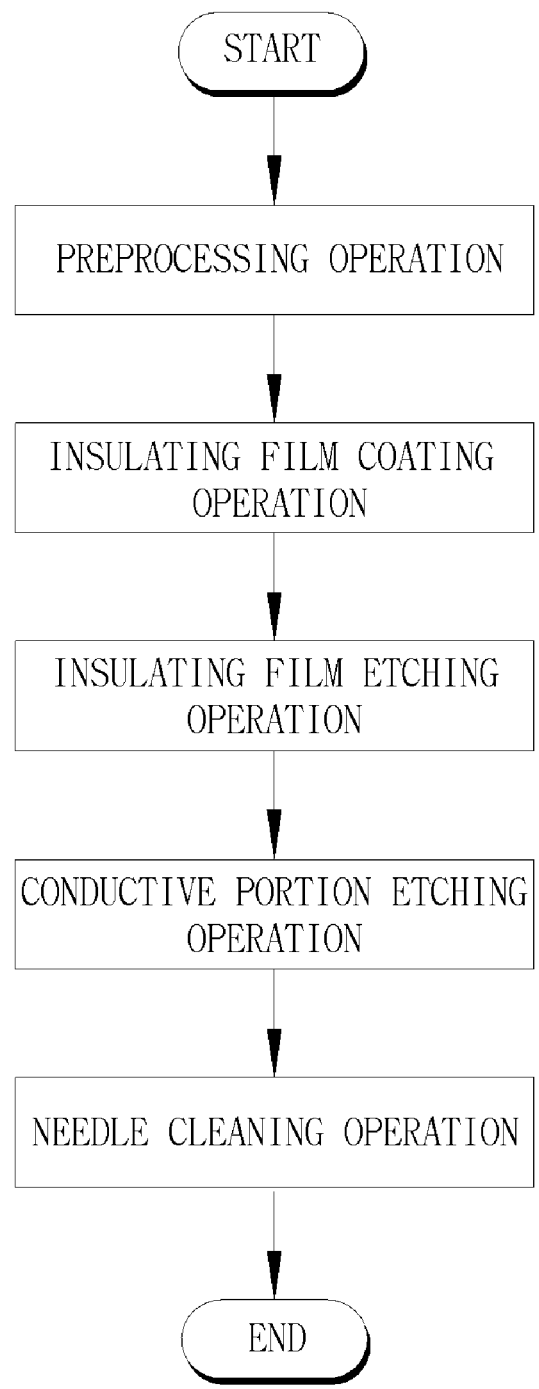
FIG. 9 is a flowchart for explaining a method of manufacturing a skin treatment needle according to the first embodiment.

FIG. 9 is a flowchart for explaining a method of manufacturing a skin treatment needle according to the first embodiment.

As illustrated in FIG. 9, the skin treatment needle according to the first embodiment of the present invention is manufactured by performing a preprocessing operation, an insulating film coating operation, an insulating film etching operation, a conductive portion etching operation, and a needle cleaning operation.

In the pre-processing operation, a rod-shaped needle body 110 having a pointed front end 110a purchased or manufactured in advance is cleaned with water and an acid cleaning liquid and then dried.

In the insulating film coating operation, the preprocessed needle body 110 is coated with an insulating film 120. The coating of the preprocessed needle body 110 with the insulating film 120 may be performed by chemical vapor deposition. A material of the insulating film 120 may be parylene or Teflon, which is harmless to humans.

In the insulating film etching operation, the insulating film 120 is removed from a predetermined region of the needle body 110 to form a conductive portion 110b. To this end, when the insulating film 120 is removed by performing etching in a circumferential direction of the needle body 110, an outer circumferential surface of the needle body 110 is exposed to form the conductive portion 110b. In the insulating film etching operation, the insulating film 120 may be easily removed by loosening the adhesion of the insulating film 120 to the needle body 110 by applying heat energy to the insulating film 120 prior to performing micromachining etching. The formation of the conductive portion 110b by partially removing the insulating film 120 may be performed preferably by micromachining but may be performed by various other methods.

In the conductive portion etching operation, a plurality of corrugations 111 are formed by micromachining etching while rotating the conductive portion 110b by 360 degrees about the outer peripheral surface of the needle body 110 exposed in a region of the conductive portion 110b. In this case, concave semicircular corrugation valleys 111a are consecutively formed by micromachining to be adjacent to each other without being spaced apart from each other, such that connecting lines 111b between the corrugation valleys 111a protrude sharply. As described above, a higher-intensity electric field may be formed at multiple points via the sharply projecting connecting lines 111b.

In the needle cleaning operation, residues occurring during the micromachining etching of the insulating film 120 and the needle body 110 are removed.

Next, various other embodiments will be described below. For reference, the same reference numerals are assigned to parts or components corresponding to those of the first embodiment.

Second Embodiment

Figure 10:
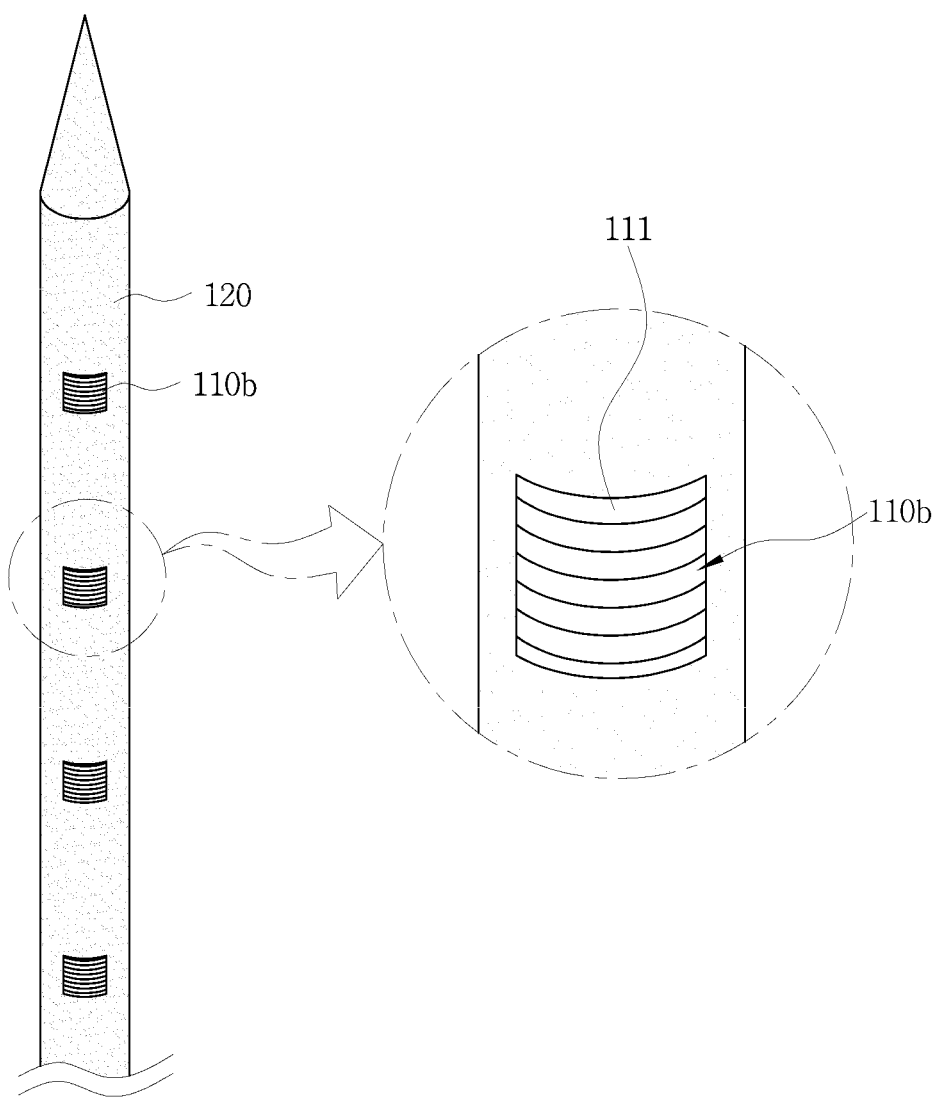
FIG. 10 is a perspective view of a skin treatment needle according to a second embodiment of the present invention.
Figure 11:
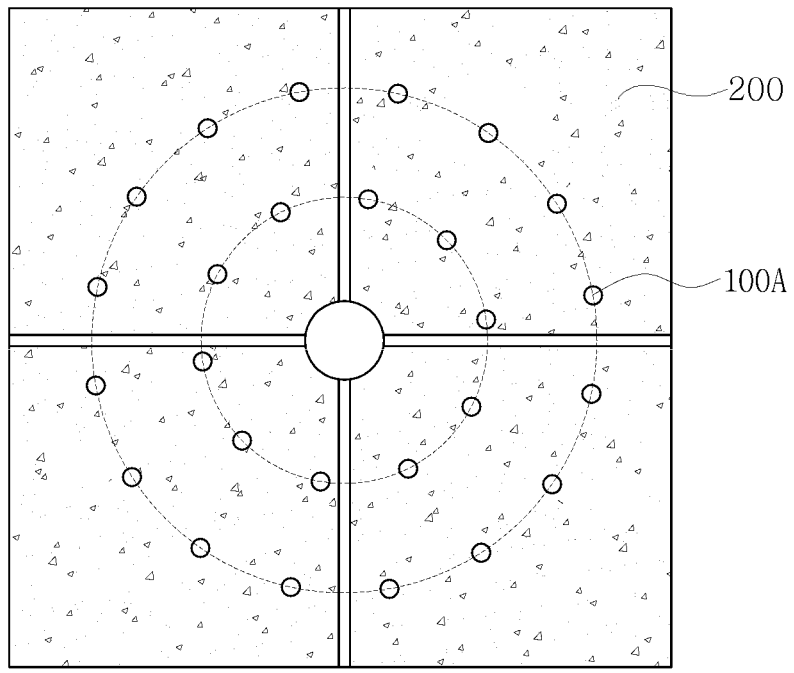
FIGS. 11 and 12 are bottom views for explaining skin treatment devices to which the skin treatment needle according to the second embodiment is applied.
Figure 12:
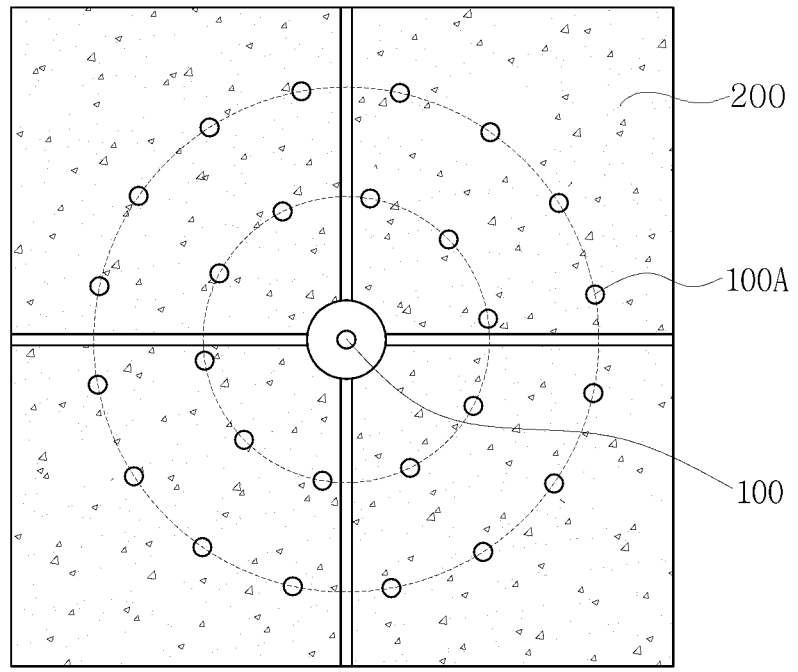

FIG. 10 is a perspective view of a skin treatment needle according to a second embodiment of the present invention. FIGS. 11 and 12 are bottom views for explaining skin treatment devices to which the skin treatment needle according to the second embodiment of the present invention is applied.

As shown in the drawings, when compared with the first embodiment, the needle according to the second embodiment is a directional needle 100A, in which a conductive portion 110b with corrugations 111 is formed only in one direction of an outer circumferential surface of a needle body 110 to have directionality, instead of being formed along the entire outer circumferential surface of the needle body 110 in the 360-degree circumferential direction.

According to a configuration of the second embodiment, conductive portions 110b of all needles 100A may be disposed to face an affected area of the skin when a needle array of a skin treatment device is configured, and thus energy may be more intensively applied to the affected area of the skin to perform a high-level treatment.

For example, the skin treatment device illustrated in FIG. 11 has a unique structure, in which needles installed on a lower installation surface of a support member 200 are directional needles 100A, and conductive portions 110b are directed toward a central portion of the skin at which an affected area is located in a state in which the directional needles 100A are arranged around the central portion of the skin. According to this configuration, the conductive portions 110b of all the directional needles 100A are directed toward the center of the installation surface of the support member 200 and thus energy may be intensively applied to the affected area.

Although the needle body 110 is illustrated in the drawings as being formed solidly, the needle body 110 may be hollow for the purpose of drug injection or the like. The needle body 110 preferably has a cylindrical shape as illustrated in the drawings but is not limited thereto and may have a prism shape having a polygonal cross section. Particularly, in the case of the second embodiment, the directional needle 100A is provided and thus the needle body 110 preferably has a prism shape in terms of the arrangement of the directional needle 100A toward a specific direction.

The skin treatment device of FIG. 12 is different from that of FIG. 11, in that, although directional needles 100A are installed around a center of an installation surface of a support member 200 as illustrated in FIG. 11 such that conductive portions 110b are directed toward the center of the installation surface, a non-directional needle 100 is provided on the center of the installation surface. A combination of the directional needles 100A and the non-directional needle 100 is advantageous when an affected area of the skin is relatively large, because the non-directional needle 10 may be inserted into a center of the affected area.

Other components of the second embodiment which are not described here are substantially the same as those of the first embodiment and thus a detailed description thereof will be omitted here.

Third Embodiment

Figure 13:
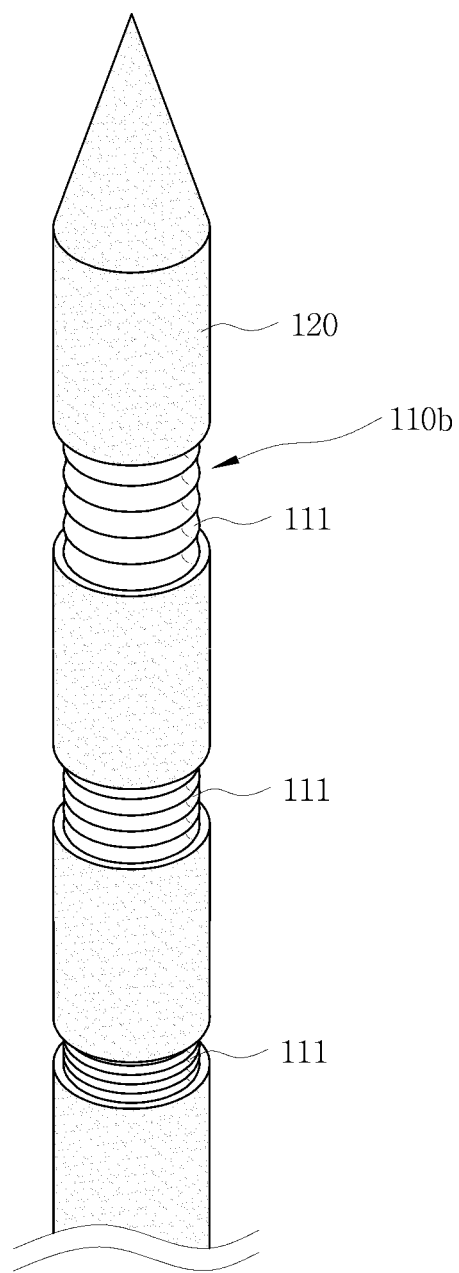
FIG. 13 is a perspective view of a skin treatment needle according to a third embodiment of the present invention.
Figure 14:
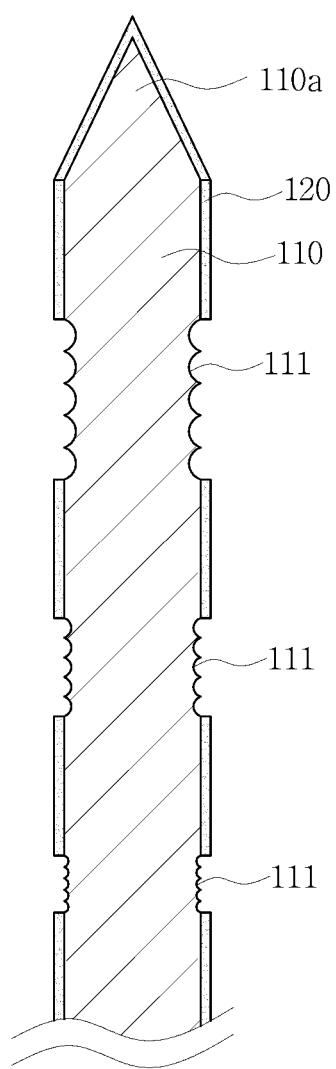
FIG. 14 is a longitudinal sectional view of a skin treatment needle according to a third embodiment of the present invention.

FIG. 13 is a perspective view of a skin treatment needle according to a third embodiment of the present invention. FIG. 14 is a longitudinal sectional view of the skin treatment needle according to the third embodiment of the present invention.

As illustrated in the drawings, when compared with the first embodiment, in the needle according to the third embodiment, a plurality of conductive portions 110b with corrugations 111 are formed on an outer circumferential surface of a needle body 110 to be spaced apart from each other, a needle body 110 is formed such that a longitudinal width thereof increases toward a front end 110a from a rear end, and a depth of corrugation valleys 111a also increases toward the front end 110a from the rear end, sand thus a stronger electric field may be formed when the needle is inserted more deeply into the skin.

According to the configuration of the third embodiment described above, higher energy may be applied by forming a relatively strong electric field via a portion of the needle that is deeply inserted into the skin, whereas lower energy may be applied near the epidermal layer of the skin by narrowly forming a relatively weak electric field. Accordingly, a treatment may be implemented while changing an intensity thereof, such that the treatment is more intensively performed deep inside the skin but the vicinity of the epidermal layer of the skin directly exposed to the outside hardly shows a sign of the treatment. Accordingly, the epidermal layer exposed to the outside may recover most rapidly after the treatment.

Other components of the third embodiment which are not described here are substantially the same as those of the first embodiment and thus a detailed description thereof will be omitted here.

Fourth Embodiment

Figure 15:
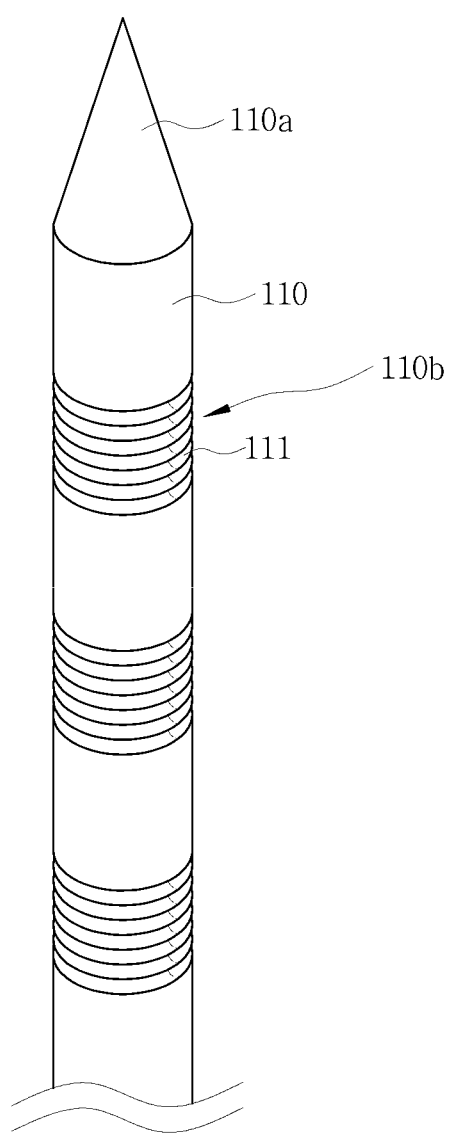
FIG. 15 is a perspective view of a skin treatment needle according to a fourth embodiment of the present invention.
Figure 16:
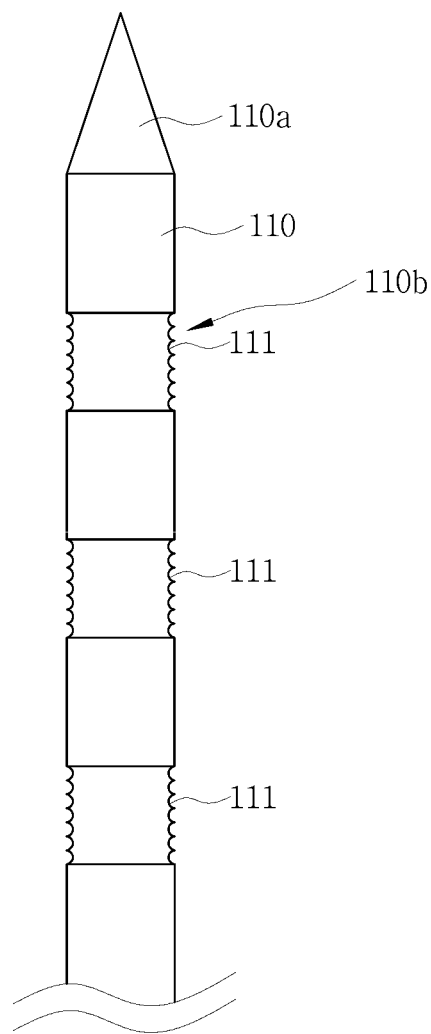
FIG. 16 is a side view of the skin treatment needle according to the fourth embodiment of the present invention.

FIG. 15 is a perspective view of a skin treatment needle according to a fourth embodiment of the present invention. FIG. 16 is a side view of the skin treatment needle according to the fourth embodiment of the present invention.

As shown in the drawings, when compared with the first embodiment, the needle according to the fourth embodiment does not include the insulating film 120, and corrugations 111 are formed by directly etching an outer circumferential surface of a needle body 110 by micromachining. In the fourth embodiment, a conductive portion 110b is a region provided with the corrugations 111.

According to the configuration of the fourth embodiment described above, a manufacturing method is simplified, because a process of forming the insulating film 120 and a separate process of forming the conductive portion 110b are not necessary in a manufacturing process, and two times of performing micromachining etching is reduced to one time.

However, in the case of the configuration according to the fourth embodiment, intensities of electric fields formed via the conductive portion 110b of the needle body 110 and other portions thereof are not high and thus there are difficulties applying higher intensity energy to a specific location in the skin than to other portions of the skin according to a purpose of a treatment.

Other components of the fourth embodiment which are not described here are substantially the same as those of the first embodiment and thus a detailed description thereof will be omitted here.

Fifth Embodiment

Figure 17:
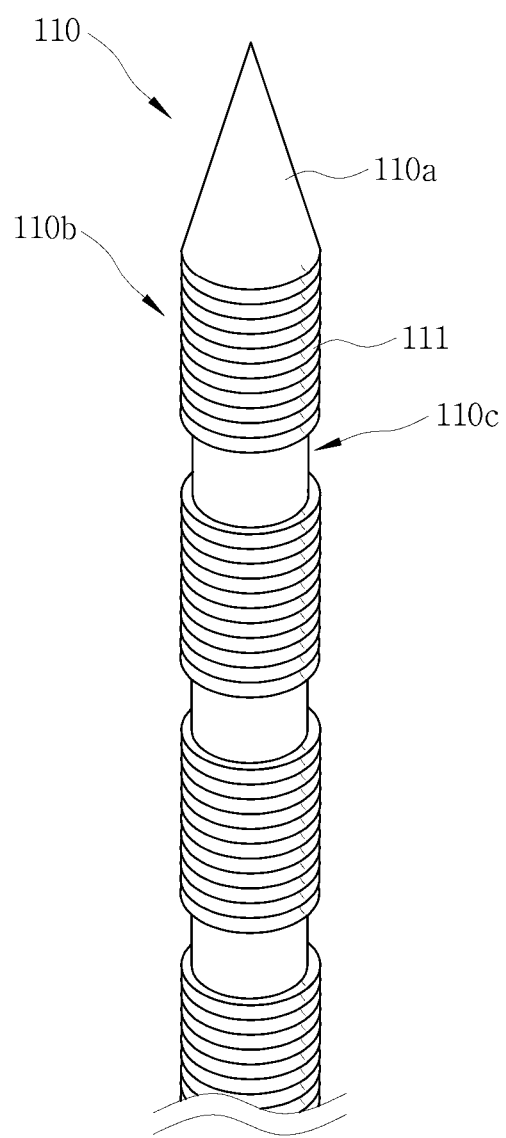
FIG. 17 is a perspective view of a skin treatment needle according to a fifth embodiment of the present invention.
Figure 18:
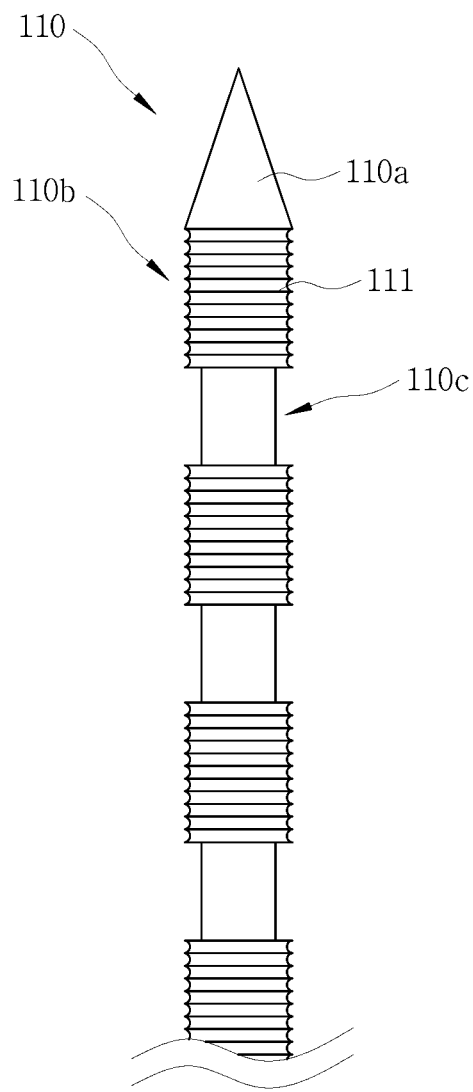
FIG. 18 is a side view of the skin treatment needle according to the fifth embodiment of the present invention.

FIG. 17 is a perspective view of a skin treatment needle according to a fifth embodiment of the present invention. FIG. 18 is a side view of the skin treatment needle according to the fifth embodiment of the present invention.

As illustrated in the drawing, the needle according to the fifth embodiment is configured to compensate for the above problem of the fourth embodiment, in which a concave portion 110c which is recessed is formed on an outer circumferential surface of a needle body 110 by performing etching using micromachining. A remaining protruding portion of the needle body 110 after the formation of the concave portion 110c is naturally configured as a conductive portion 110b. Here, the conductive portion 110b and the concave portion 110c are alternately provided in a longitudinal direction of the needle body 110.

The concave portion 110c is formed to have a longitudinal width of about 100 to 300 micrometers, and is brought into contact with the skin at lower contact strength than the conductive portion 110b having a protruding shape.

A plurality of corrugations 111 formed by secondary micromachining etching are provided on a surface of the conductive portion 110b. The corrugations 111 of the conductive portion 110b are provided with corrugation valleys 111a having a depth of 5 to 15 micrometers.

When the needle according to the fifth embodiment is inserted into the skin, both the concave portion 110c and the conductive portion 110b are brought into direct contact with the skin at different contact strengths, thereby achieving different effects. In this case, the conductive portion 110b applies energy by an electric field while in stronger contact with the skin than the concave portion 110c. In this case, although the conductive portion 110b protrudes, the corrugations 111 uniformly disperse the electric field and thus the electric field may be prevented from being excessively concentrated at the edges of the conductive portion 110b.

In the fifth embodiment, the conductive portion 110b is formed along the outer circumferential surface of the needle body 110 to surround the needle body 110 in a 360-degree circumferential direction, similar to the first embodiment, but it may be formed to be oriented in one direction, similar to the second embodiment. To this end, the conductive portion 110b, which is formed in a ring shape by additional etching during the etching of the concave portion 110c, may be reduced to an island shape oriented in one direction as in the second embodiment.

Alternatively, the fifth embodiment may be modified such that a longitudinal width of a plurality of conductive portions 110b and a depth of the corrugation valleys 111a increase from the rear end of the needle body 110 toward the front end 110a, so that a stronger electric field may be formed as a depth of insertion into the skin increases.

Other components of the fifth embodiment which are not described here are substantially the same as those of the previous embodiments and thus a detailed description thereof will be omitted here.

Sixth Embodiment

Figure 19:
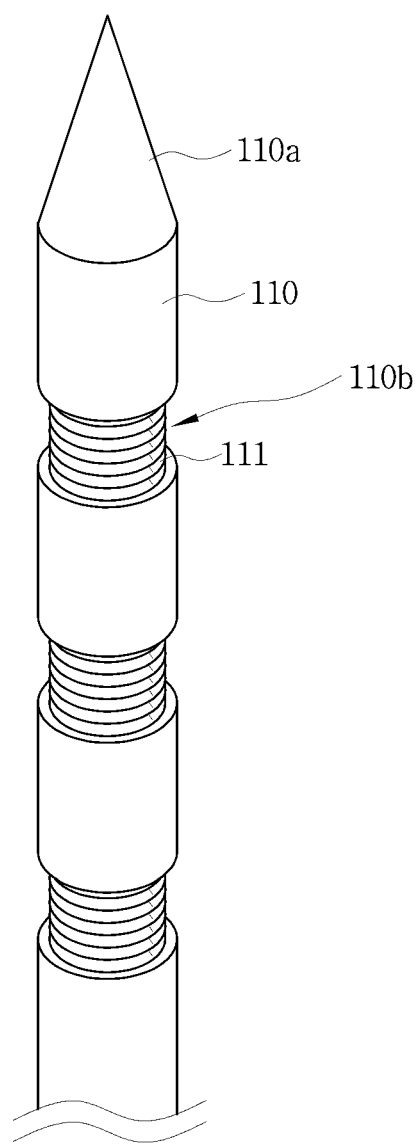
FIG. 19 is a perspective view of a skin treatment needle according to a sixth embodiment of the present invention.
Figure 20:
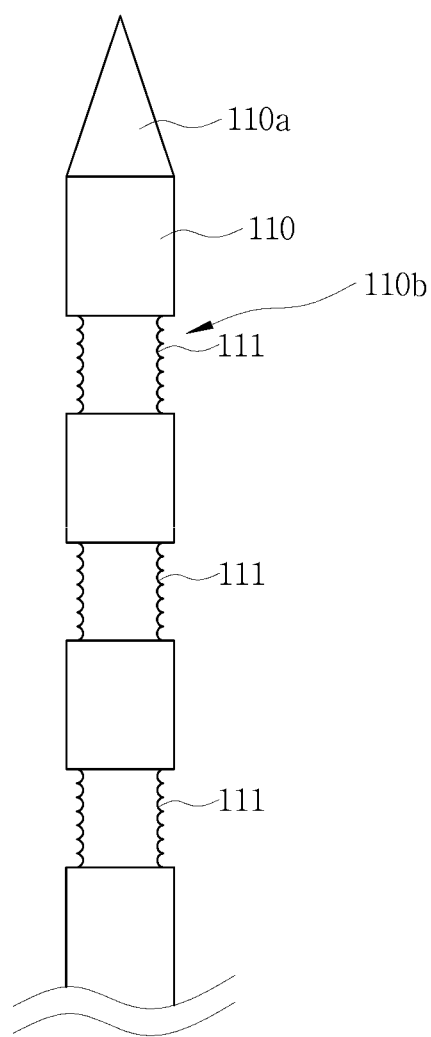
FIG. 20 is a side view of the skin treatment needle according to the sixth embodiment of the present invention.

FIG. 19 is a perspective view of a skin treatment needle according to a sixth embodiment of the present invention. FIG. 20 is a side view of the skin treatment needle according to the sixth embodiment of the present invention.

As illustrated in the drawing, the needle according to the sixth embodiment is different from that of the fifth embodiment in that a conductive portion 110b is recessed rather than protruding. In this case, etching is performed by micromachining to form the conductive portion 110b that is recessed.

The conductive portion 110b is formed to have a longitudinal width of 100 to 300 micrometers, and a plurality of the conductive portions 110b are provided on an outer circumferential surface of a needle body 110 to be spaced apart from each other. A surface of the conductive portion 110b is provided with a plurality of corrugations 111 formed by secondarily performing micromachining etching. The corrugations 111 of the conductive portion 110b are provided with corrugation valleys 111a having a depth of 5 to 15 micrometers. The conductive portion 110b may be brought into contact with the skin at lower contact strength than other portions of the needle.

In the case of the needle of the sixth embodiment, the conductive portion 110b applies energy by an electric field while in contact with the skin at lower contact strength than other portions. In this case, the corrugations 111 of the conductive portion 110b uniformly distribute an electric field and thus the electric field may be prevented from being excessively concentrated on edges of ends of the conductive portion 110b.

In the sixth embodiment, the conductive portion 110b is formed along the outer circumferential surface of the needle body 110 to surround the outer circumferential surface of the needle body 110 in a 360-degree circumferential direction, similar to the fifth embodiment. Alternatively, the sixth embodiment may be modified such that the conductive portion 110b is formed to have directionality in one direction, similar to the second embodiment, or such that a longitudinal width of a plurality of conductive portions 110b increases from a rear end of the needle body 110 toward a front end 110a thereof and a depth of the corrugation valleys 111a increases from the rear end of the needle body 110 toward the front end 110a thereof so that a stronger electric field may be formed as a depth of insertion into the skin increases, similar to the third embodiment.

Other components of the sixth embodiment which are not described here are substantially the same as those of the previous embodiments and thus a detailed description thereof will be omitted here.

While the exemplary embodiments of the present invention have been described above, various modifications, changes, and equivalents may be made therein. It is clear that the above embodiments of the present invention may be appropriately modified and applied similarly. Accordingly, the scope of the present invention defined in the claims should not be understood as being limited by the above description.

The invention claimed is:

1. A skin treatment needle by which energy is supplied into skin tissue to increase a speed of skin regeneration, the skin treatment needle comprising a needle body that is formed of a conductive material and adapted to be inserted into skin, starting from a front end thereof,
wherein a region of an outer circumferential surface of the needle body comprises a conductive portion which is a region inducing an electric field, and
wherein the conductive portion comprises a plurality of corrugations to cause an electric field formed via the conductive portion to have a uniform distribution,
wherein the conductive portion is formed to be recessed by micromachining etching the outer circumferential surface of the needle body, wherein the conductive portion is provided with a plurality of conductive portions that are arranged to be spaced apart from each other in a longitudinal direction of the needle body, and
a depth of corrugation valleys formed in the conductive portions is in a range of 5 to 15 micrometers.

2. The skin treatment needle of claim 1, further comprising an insulating film coated with an insulating material, the insulating film being provided on a remaining portion of the outer circumferential surface of the needle body aside from the conductive portion.

3. The skin treatment needle of claim 2, wherein the insulating film is formed of parylene.

4. The skin treatment needle of claim 2, wherein the corrugation valleys are formed by performing micromachining etching, the corrugation valleys having a depth of less than or equal to ¼ of a diameter of the needle body.

5. The skin treatment needle of claim 4, wherein the depth of the corrugation valleys is in a range of 5 to 15 micrometers.

6. The skin treatment needle of claim 1, wherein the conductive portion is provided with one conductive portion or a plurality of conductive portions which are arranged to be spaced part from each other on the outer circumferential surface of the needle body from the front end of the needle body to a rear end thereof.

7. The skin treatment needle of claim 6, wherein the conductive portions are provided in a 360-degree circumferential direction of the outer circumferential surface of the needle body.

8. The skin treatment needle of claim 6, wherein the conductive portions are provided on a half or less than a half portion of the outer circumferential surface of the needle body in a circumferential direction of the outer circumferential surface of the needle body to have directionality.

9. A skin treatment device by which energy is supplied into skin tissue via needles to increase the speed of skin regeneration, the skin treatment device comprising:
   a support member; and
   a plurality of needles identical to claim 1, the plurality of needles being provided at a lower portion of the support member to be inserted into skin, starting from front ends thereof.

10. A skin treatment needle by which energy is supplied into skin tissue to increase a speed of skin regeneration, the skin treatment needle comprising a needle body that is formed of a conductive material and adapted to be inserted into skin, starting from a front end thereof,
   wherein a region of an outer circumferential surface of the needle body comprises a conductive portion which is a region inducing an electric field,
   wherein the conductive portion comprises a plurality of corrugations to cause an electric field formed via the conductive portion to have a uniform distribution, and
   wherein the skin treatment needle further comprises:
   a concave portion formed by micromachining etching a remaining portion of the outer circumferential surface of the needle body, aside from a portion at which the conductive portion is to be formed, to form the conductive portion in a protruding form, the concave portion being relatively recessed,
   wherein a plurality of conductive portions identical to the conductive portion and a plurality of concave portions identical to the concave portion are alternately arranged in a longitudinal direction of the needle body, the plurality of conductive portions and the plurality of concave portions each having a longitudinal width of 100 to 300 micrometers, and
   a depth of corrugation valleys formed in the plurality of conductive portions is in a range of 5 to 15 micrometers.

11. A skin treatment needle by which energy is supplied into skin tissue to increase a speed of skin regeneration, the skin treatment needle comprising a needle body that is formed of a conductive material and adapted to be inserted into skin, starting from a front end thereof,
   wherein a region of an outer circumferential surface of the needle body comprises a conductive portion which is a region inducing an electric field,
   wherein the conductive portion comprises a plurality of corrugations to cause an electric field formed via the conductive portion to have a uniform distribution,
   wherein the conductive portion is provided with a plurality of conductive portions which are spaced apart from each other on the outer circumferential surface of the needle body, and
   wherein a longitudinal width of the conductive portions and a depth of corrugation valleys increase toward the front end of the needle body from a rear end thereof to form a stronger electric field as a depth of insertion into the skin increases.

12. A skin treatment needle by which energy is supplied into skin tissue to increase a speed of skin regeneration, the skin treatment needle comprising a needle body that is formed of a conductive material and adapted to be inserted into skin, starting from a front end thereof,
   wherein a region of an outer circumferential surface of the needle body comprises a conductive portion which is a region inducing an electric field,
   wherein the conductive portion comprises a plurality of corrugations to cause an electric field formed via the conductive portion to have a uniform distribution, and
   wherein the corrugations comprise concave semicircular corrugation valleys consecutively formed and connecting lines between the corrugation valleys to form a high-intensity electric field at a plurality of positions via the connecting lines, the connecting lines having a protruding peaked form.

* * * * *